United States Patent [19]

Ando et al.

[11] Patent Number: 4,622,263
[45] Date of Patent: Nov. 11, 1986

[54] WATER ABSORBING WEBS

[75] Inventors: Katsutoshi Ando; Eiichi Nishiura, both of Otsu; Yoshiyuki Yamamoto, Suzuka, all of Japan

[73] Assignee: Toray Industries, Inc., Tokyo, Japan

[21] Appl. No.: 733,949

[22] Filed: May 14, 1985

[30] Foreign Application Priority Data

May 15, 1984 [JP] Japan .................................. 59-97366

[51] Int. Cl.$^4$ .............................................. D04H 1/58
[52] U.S. Cl. .................................... 428/288; 428/296; 428/913; 604/370
[58] Field of Search ................ 604/370; 428/296, 913, 428/392, 394, 364, 288

[56] References Cited

U.S. PATENT DOCUMENTS 4,148,960  4/1979  Yung et al. ........................... 428/296

FOREIGN PATENT DOCUMENTS 0123545  10/1984  European Pat. Off. .
42978    3/1982   Japan .
89642    6/1982   Japan .

*Primary Examiner*—James J. Bell
*Attorney, Agent, or Firm*—Austin R. Miller

[57] ABSTRACT

This invention relates to a melt-blow water-absorbing fiber webs whose main component is block-copolyetheresters having polyester and polyether segments in the molecules, wherein the amount the polyether component is 5 to 80 wt % base on the block-copolyetheresters.

The water-absorbing web of this invention shows high chlorine fastness and consequently shows excellent water absorption performances after repeated washing. They are available as good batting (urine absorber) for diapers, as well as bed pads, towel materials and sports underpants, and applicable to a wide range of disposal products which require high water absorption performances and durability.

12 Claims, No Drawings

WATER ABSORBING WEBS

FIELD OF THE INVENTION

This invention relates to water-absorbing webs, especially those manufactured from melt-blow fiber webs having high chlorine fastness (chlorine bleaching resistance).

Hitherto water-absorbing fibers have commonly been manufactured from cotton, wool, hemp and so forth. However, they have such problems that they are short of chlorine fastness and shrinkage in washing. They degrade seriously when being washed repeatedly under such severe conditions as imposed on lease diapers, for example, washing for 30 to 60 minutes at 70° to 80° C. in an aqueous solution of 0.03 to 0.05 percent sodium hypochlorite, about 0.03 percent detergent and dirty oily substances.

Though polyester fibers are widely used, they are inferior to cotton, wool, hemp and so forth in water-absorption performance because of their hydrophobicity. Various methods have been proposed for their improvement in these respects.

Laid-Open Pat. No. 89642/1982 proposes the use of polyester fibers of less than 1.5 deniers and have, on their surface, fine pores with the diameters of 0.01 to 3 μm and the depth of less than 50 times of the diameters.

Laid-Open Pat. No. 42978/1982 proposes the processes for copolymerizing the hydrophilic compounds on fiber surface.

These fibers show a considerable durability against repeated (for example 50 times) washing under mild conditions such as household washing.

In the former's case, however, polyester fibers decrease in hydrophilicity because the surface pores disappear through hydrolysis or plugging with dirty substances during repeated washing of more than 100 times under such severe conditions as stated above and successive drying at the temperatures of 80° to 120° C. for 30 minutes.

In the latter's case, on the other hand, surface analysis has shown that polyester fibers become hydrophobic through falling out or decomposition of the surface layer or gradual oil deposit on unmodified part of the fiber surface. Namely, they lose water absorption performance through the repeated washing of 30 to 50 times under severe conditions.

The purpose of this invention is to present water-absorbing polyester type webs having high durabilities against washing under severe conditions.

SUMMARY OF THE INVENTION

The purpose of this invention is attainable by the melt-blow water-absorbing fiber webs whose main component is block-copolyetheresters having polyester and polyether segments in the molecules, characterized in that the amount the polyether component is 5 to 80 wt % based on the weight of block-copolyetheresters.

DETAILED DESCRIPTION OF THE INVENTION

The block-copolyetherester of this invention can be obtained by copolymerization of dicarboxylic acid, a short chain diol and polyetherglycol. The dicarboxylic acid and the short chain diol forms the polyester segment and the polyether glycol forms the polyether segment in the block copolyether ester.

The dicarboxylic acids include terephthalic acid, isophthalic acid, 2,6-naphthalenedicarboxylic acid, 1,5-naphthalenedicarboxylic acid, diphenyl-p-p'-dicarboxylic acid, bis(p-carboxyphenyl)methane and adipic acid. The short chain glycols include ethylene glycol, 1,2- and 1,3-propylene glycols, 1,3- and 1,4-buthane diols, neopentyl glycol, 1,5-pentane diol, 1,6-hexane diol, decamethylene diol and diethylene glycol, cycloalkylene glycols include 1,3- and 1,4-cyclohexanedimethanols, and allylalkylene glycols include p-dihydroxymethylbenzene, m-dihydroxymethylbenzene and 2,2-di(p-hydroxyphenyl)propane and so forth.

The polyester segments being manufactured from dicarboxylic acids and diols include polyethylene and polybutylene terephthalates, polybutylene isophthalate, polybutylene adipate, poly(1,6-hexamethylene terephthalate), poly(ethylene-2,6-naphthalates), poly(butylene-2,6-naphthalate) and poly(1,4-cyclohexylenemethylene terephthalate).

The polyether glycols used in this invention are for example, polyethylene glycol, poly(1,2- and 1,3-propylene oxide) and poly(alkylene oxide) glycols. They are copolymerized with dicarboxylic acid and short chain diol by ordinary methods. It is important that the polyether contents of 5 to 80 wt % are based on the weight of the polyetherester.

The polyetherester or its mixtures with other organic polymers are melt-blown by a known method to form webs. Preferable among block-copolyetheresters are those being composed of terephthalic acid, 1,4-buthane diol and polyethylene glycol, and the polymers prepared by replacing part of terephthalic acid with isophthalic or adipic acid. Polyethylene glycol to be used should have the molecular weights of 200 to 20,000, preferably of 400 to 6,000. The block-copolyetheresters polymers to be used alone should have the polyether contents of 5 to 80 wt %. For better chlorine fastness and durability under severe washing conditions, they should be 5 to 30 wt %, preferably at 8 to 20 wt %.

Any organic polymers may be blended with block-copolyetheresters, provided they are easy to mix with the latter and stable at the temperature of the melt-blow. They should preferably be resistant to hot water, to oxidation by sodium hypochlorite and to drying temperature after repeated washing. For example, polymers such as polybutylene terephthalate and coplymers thereof, water absorbing polymers such as polyalkylene glycol, or a mixture of a block-copolyester and alkylbenzene sulfonate, or poly(alkylene oxide) glycol are preferable.

When other polymers are blended with block-copolyetheresters, the polyether content in the latter should be at 5 to 80 wt %. More desirably it should be 40 to 80 wt % and, based on the total weight of the mixture, it should be 8 to 20 wt %.

Polyalkylene glycol, alkylbenzene sulfonate and poly(alkylene oxide) glycol can be blended with block-copolyetheresters. Particularly polyethylene glycol, dodecylbenzenesulfonate and poly(alkylene oxide) glycol should preferably be blended at the ratios of 1 to 10 wt %. In this case, it is particularly preferable to fix the polyether content in the total mixtures at 5 to 20 wt %. These components can partly react with the polyetherester through ester exchanging during melt-blowing or endow fibers with fine pores by dissolving out during washing.

Composed of 0.05 to 0,8 denier superfine filaments, the melt blow webs of this invention have high heat insulation performances. On the other hand, for practical purposes, heat stabilizers (antioxidants) should preferably be used in combination therewith since polyalkylene glycol is susceptible to thermal decomposition, often together with spontaneous combustion.

Among heat stabilizers, hindered phenol type such as 1,3,5,-tris(4-t-butyl-3-hydroxy-2,6-dimethylbenzyl)isocynulate (CYANOX 1790: American Cyanamid Co.), pentaerythrityl-tetrakis(3-(3,5-di-t-butyl-4-hydroxyphenyl)propionate) (IRGANOX 1010: CIBA-GEIGY Ltd.) or 1,3,5-tris(3,5-di-t-butyl-4-hydroxybenzyl)benzene (IRGANOX 1330: CIBA GEIGY Co.), phosphite type such as reaction product between calcium carboxylate and phosphorous acid, distearyl-pentaerythritol-diphosphite, dinonylphenylpentaerythritol-diphosphite and thioether type such as distearylthiodipropionate, diraurylthiodipropionate are preferable. They can be used alone or as mixtures thereof and should be added at the ratios of 0.05 to 10 wt %, preferably at 0.2 to 7 wt % based on the total weight of the polymers.

These stabilizers can be added either at or after polymerization or at spinning procedure. Some of them can becomes in the block-copolyetheresters. If its ratio is less than 0.05 percent, its effects are insufficient and, heat generation becomes probable after repeated washing. If it is more than 10 wt %, fibers forming properties become unsatisfactory.

It is important for water-absorbing webs of this invention to be composed of the fibers having the average size of 0.05 to 0.8 deniers. Such fiber web can be easily obtained by melt-blow method, fiber forming by air jet, for example, described in European Patent Application Publication No. 123,545. If the average fiber size is below 0.05 deniers, water absorption performances are improved but fiber length becomes too short to cause the web breakage in repeated washing. If they are above 0.8 deniers, the spaces between fibers become large to cause the decrease in water holding capacity and, furthermore, the web become hard because the melt-blow fibers have large denier distribution and they have considerable-amount of large-denier fibers therein.

Because of such a construction as described heretofore, the water absorbing webs of this invention have high water absorption performances and good durability against repeated washing in which chlorine compound is used. They are available as good batting (urine absorbor) for diapers, as well as bed pads, towel materials and sports underpants, and applicable to a wide range of disposal products which require high water absorption performances.

Further, the polymers of this invention can be meltspun by the ordinary melt spinnings to make woven or knitted fabric which has water absorption performance.

In this case the polymers are usable either alone or as a component of composite fibers.

This invention will be described further with examples hereinafter. The following are the methods for evaluating their water absorption performance, washing resistance and mean fiber size.

(Water absorption performance)

(1) Water absorption rate, method A:

According to JIS L 1079, five 20×20 sample pieces were clamped to metal rings so that they do not slacken. Next 1 cc of the distilled water at the temperatures of 20° C.±2° C. was dripped from a burrette onto test webs from above 1 cm of the web. With a stop watch being set in operation immediately thereafter, the time until mirror reflection disappeared with water drops being absorbed was measured. Water absorption rate was represented by the mean value of the measured times.

(2) Water absorption rate, method B:

Five test pieces having a radius of 15 cm were prepared and each test piece was set like filter paper in a glass funnel having a radius of 11 cm with part of their fourfolding being opened and a 500 cc measuring cylinder was set in the lower part of the glass funnel. Using another 200 cc measuring cylinder, 200 cc of the distilled water at the temperatures of 20° C.±2° C. is supplied to the set test pieces. With a stop watch started immediately thereafter, the time until the supplied water absorbed was measured. Water absorption rate was represented by the mean value of this measurement for the five test pieces.

(3) Water holding capacity, method A:

In the absorption rate, method B, the volume difference between the amount of the water supplied and the amount of the water fallen into a lower measuring cylinder was determined. Their water holding capacity was represented by the mean value of the volume differences for the five test pieces.

(4) Water holding capacity, method B:

Five 10 cm×10 cm pieces were sampled and left in an atmosphere at the temperatures 20° C.±2° C. and the humidities of 65±2 wt % for 24 hours and their weight was measured.

The samples were kept immersed in the distilled water at the temperatures of 20° C.±2° C. for 30 minutes. They were sandwiched between 2 mm-thick 10×10 cm aluminum plates having 41 holes of 3 mm bored at equal intervals and left for three minutes under 10 kg load. After dewatering, their weight was measured and their water holding capacity magnification was calculated using equation:

$$\text{Water holding capacity} = \frac{\text{weight after dewatering}}{\text{weight after moisture control}}$$

It was represented by the mean value of the five pieces.

(Washing resistance)

(1) Washing, method A:

Intensified reciprocatory rolling washing was continued at a temperature of 40° C. using Toshiba VH-9500 washer with bath ratio being fixed at 30:1 by supplying 30 l water containing 0.03 percent industrial detergent and 0.03 percent sodium hypochlorite. Washing was continued for 15 minutes by intensified reciprocatory rolling. Dehydration was continued for 3 minutes and after 10 minutes over-flow rising, 3 minutes dehydration was conducted again. Drying was continued for 20 minutes with Osaka Gas (N) 60–004A(U) tumbler drier being set to a high-temperature graduation. These steps constituted one cycle of washing.

(2) Washing, method B:

Washing was carried out under the conditions shown in the following washing process table using Kotobuki Kogyo K.K.'s washer for industrial use (NSLW-380) and the same manufacturer's oil-water dehydrator HE-160 and the tumbler drier in the order of mention. These steps constituted one cycle of washing.

|  | Pre-washing | Pre-washing | Washing | Rinsing | Rinsing | Rinsing | Rinsing |
|---|---|---|---|---|---|---|---|
| Time (min.) | 4 | 4 | 20 | 4 | 4 | 4 | 4 |
| Water quantity (t) | 1.7 | 1.5 | 0.5± | 1.5 | 1.5 | 1.5 | 1.5 |
| Temperature (°C.) | 50 | 51 | 80 | 50 | 50 | 50 | 50 |

Detergent: Soap 4 kg
Sodium metasilicate type auxilliary 1.5 kg
Aqueous solution of sodium hypochlorite 6 l (3) Washing, method C:

Washing was continued for 20 minutes with 60 l of hot water containing 0.03 percent sodium hypochlorite and 0.03 percent detergent using water washing tester (LM-W1) (supplied by Suga Tester K.K. ) and rolling being reversed in 15 seconds (intermediate stop 2.5 seconds). This step as well as 10 minutes' overflow rinsing, centrifugal dehydration and tumbler drying constituted one cycle of washing.

(Mean fiber size)

250 filaments were randomly sampled from fiber webs and their fiber size (diameter) distribution was diagrammed using a scanning electron microscope. Their mean fiber size was represented by the top of the nearly-normal distribution of this diagram.

EXAMPLE 1

Poly-1,4-butylene terephthalate was prepared from dimethyl terephthalate and 1,4-butane diol by an ordinary method Block-copolyetheresters were manufactured with dimethyl terephthalate and 1,4-butane diol and the polyethylene glycol (PEG-4000) having a molecular weight of 4,000, and after polymerization 0.5 and 1.0 wt % of CYANOX 1790 based on the block-copolyetherester were added as heat stabilizer. Polyester/polyether segment ratios by weight were fixed at 100/0 (No. 1), 95/5 (No. 2), 90/10 (No. 3), 85/15 (No. 4), 80/20 (No. 5), 50/50 (No. 6) and 20/80 (No. 7), and pelletized using an extruder. Obtained pellets were vacuum-dried and spun by melt-blow method to make fiber webs so that the mean fiber sizes become 0.1 to 0.2 deniers and a weight of about 600 gr./m².

The fiber webs were sandwiched between cloths of the grey sheeting pieces of polyester textured yarn of 120 gr/m² and they were quilted by 2-inch interval. The 35 cm-wide and 1 m-long cut pieces of this cloth were subjected to the 5 cm-radius cutting-off of four corners, rimmed with the same grey sheeting as side cloths to manufacture the diapers shown in FIG. 1.

The samples of the diapers were washed by methods A and B repeatedly 100 times and their water absorbing performances and shape retention were evaluated. In method A, the side cloths were removed to avoid their influences for water absorbing performance. Evaluation conditions and results are shown in Table 1.

TABLE 1

| | Block-copolyetheresters | | Heat stabilizer | Mean fiber size (denier) | Web Weight (gr./m²) | Spinn-ability | Household washing 100 times | | | | |
|---|---|---|---|---|---|---|---|---|---|---|---|
| | | | | | | | Water absorption rate, method A | Water absorption rate, method B | Water holding-capacity method A | Water holding-capacity method B | Shape retention |
| No. | Polyester segment | Polyether segment | | | | | | | | | |
| 1 | 100% | — | — | 0.22 | 605 | Good | >180 | >180 | — | 6.4 | Good |
| 2 | 95 | 5% | 0.5 | 0.19 | 585 | Good | 4 | 18 | 110 | 6.2 | Good |
| 3 | 90 | 10 | 1.0 | 0.15 | 605 | Good | 2 | 13 | 132 | 6.7 | Good |
| 4 | 85 | 15 | 1.0 | 0.20 | 610 | Good | <1 | 12 | 126 | 6.8 | Good |
| 5 | 80 | 20 | 1.0 | 0.16 | 595 | Good | <1 | 8 | 120 | 6.1 | Slight web biasing |
| 6 | 50 | 50 | 1.0 | 0.12 | 590 | A little shot | <1 | 7 | 72 | — | Web biasing by degradation |
| 7 | 20 | 80 | 1.0 | 0.12 | 580 | Shot | <1 | — | — | — | Web breakage and biasing by degradation |
| 8 | 85 | 15 | 1.0 | 0.01 | 595 | Partial scatter of web | — | — | — | — | Web faling by degradation |
| 9 | 85 | 15 | 1.0 | 0.70 | 600 | Good | <1 | 11 | 115 | 7.2 | Good |
| 10 | 85 | 15 | 1.0 | 3.1 | 605 | Shot | <1 | 13 | 102 | 7.9 | Good but hard (texture) |
| 11 | 85 | 15 | 0 | 0.19 | 590 | Shot | <1 | 12 | 130 | 6.9 | Good |

| | Laundry washing 100 times | | | | | |
|---|---|---|---|---|---|---|
| No. | Water absorption rate, method A | Water absorption rate, method B | Water holding-capacity method A | Water holding-capacity method B | Shape retention | Remarks |
| 1 | >180 | >180 | — | 6.3 | Good | |
| 2 | >180 | >180 | — | 6.4 | Good | |
| 3 | 9 | 24 | 124 | 6.6 | Good | |
| 4 | 1 | 15 | 122 | 6.4 | Good | |
| 5 | <1 | 12 | 116 | 5.2 | Slight web biasing | |
| 6 | <1 | — | — | — | Web breakage and biasing by degradation | |
| 7 | — | — | — | — | Degradation | (Washing stopped after 50 times.) |
| 8 | — | — | — | — | Degradation | (Washing stopped after 50 times.) |
| 9 | 2 | 19 | 117 | 6.8 | Good | |
| 10 | 3 | 18 | 97 | 7.2 | Good but hard (texture) | Water moved downward when samples were left after test of water holding capacity; method B. Heat generation peak was observed |
| 11 | 1 | 16 | 126 | 6.7 | Good | |

Consequently, in washing method A that is comparable to household washing, the fiber webs having polyether segement of more than 5 wt % were useful as abosorbing web. If the segment increased to 50 and 80 wt %, the fibers and fiber webs showed too low spinnabilities and strengths for practical use. It should preferably be fixed at less than 20 wt %.

In the case of washing method B under severe conditions, on the other hand, the polyether segment of less than 5 wt % caused the decrease in water absorption performance. It should be 10 to 20 wt %, preferably 10 to 15 wt %. The diapers having the mean fiber sizes of 0.2 and 0.7 deniers were good even if the polyether segment had a ratio of 15 wt %. On the other hand, 0.01-denier one caused biasing and breakage in repeated washing. The one having a fiber size of 3 deniers was not good because it showed hard texture and water moved downward.

A commercially-available bleached cotton diaper (ringed type, duplex, weight was 170 gr./cm²) was evaluated as sixfold for comparison. Initially it was considered to be a little short of water holding capacity and give a wet feeling, showing the water absorption speed of methods A and B of less than 1 second and of 7 seconds respectively and the water holding capacity of the methods A and B of 110 cc and fifty-five times respectively, but marked sufficiently-high absorption speeds for practical use. However, it considerably degraded to break when washing method A was repeated 100 times and was not capable of retaining its shape at 50 to 60 times repeated washing of method B. Another comparative example, a 100 percent polyester segment diaper (No. 1), was tested by washing method B after immersed in "Permalose T" solution made by ICI and kept cured at a temperature of 170° C. for 15 seconds for giving hydrophilicity. They, however, became too hydrophobic for practical use after 30 repeat washings.

EXAMPLE 2

Nos. 1, 2, 4 and 6 pellets of Example 1 and a polyethylene glycol (PEG-20000) having a molecular weight of 20,000 were separately vacuum-dried and blended at the No. 6/No. 1/PEG-20000 ratios by weight of 10/90/0 (No. 12), 20/80/0 (No. 13), 50/50/0 (No. 14) and 10/85/5 (No. 15) and at the No. 1/No. 4 ratios by weight of 90/10 (No. 16) and 66.7/33.3 (NO. 17) respectively.

Diapers were prepared from these mixtures by a melt-blow method in the same manner as Example 1 and evaluated. The results of this evaluation are shown in Table 2.

TABLE 2

| | Organic polymers | | | | | | Household washing 100 times | | | |
|---|---|---|---|---|---|---|---|---|---|---|
| No. | Block-copolyetheresters (Polyester segment/Polyether segment) | Organic polymer and water absorbor | Heat stabilizer | Mean fiber size (denier) | Web Weight (gr./m²) | Spinnability | Water absorption rate, method A | Water absorption rate, method B | Water holding capacity method A | Water holding capacity method B |
| 12 | 10% (50/50) | PBT 90% | 1.0 | 0.19 | 595 | Good | 5 | 19 | 117 | 6.8 |
| 13 | 20% (50/50) | 80% | 1.0 | 0.20 | 605 | Good | 2 | 14 | 126 | 6.4 |
| 14 | 50% (50/50) | 50% | 1.0 | 0.12 | 590 | Shot | <1 | — | — | — |
| 15 | 10% (50/50) | PBT 85% PEG 5% | 1.0 | 0.17 | 595 | Good | 4 | 17 | 128 | 7.2 |
| 16 | 10% (85/15) | PBT 90% | 0.5 | 0.21 | 590 | Good | 158 | 79 | 45 | 6.7 |
| 17 | 33.3% (85/15) | PBT 66.7% | 1.0 | 0.18 | 605 | A little shot | 6 | 14 | 111 | 6.1 |
| 18 | 100% (85/15) | — | 1.0 | 0.17 | 602 | Good | <1 | 13 | 127 | 6.9 |

| | | Laundry washing 100 times | | | | |
|---|---|---|---|---|---|---|
| No. | Shape retention | Water absorption rate, method A | Water absorption rate, method B | Water holding capacity method A | Water holding capacity method B | Shape retention |
| 12 | Good | >180 | >180 | — | 6.4 | Good |
| 13 | Good | 8 | 23 | 121 | 6.3 | Good |
| 14 | Web breakage by degradation | — | — | — | — | — |
| 15 | Good | 12 | 26 | 115 | 6.5 | Good |
| 16 | Good | >180 | >180 | — | 6.3 | Good |
| 17 | Slight web biasing by degradation | >180 | >180 | — | — | Slight web biasing by degradation |
| 18 | Good | 1 | 16 | 123 | 6.6 | Good |

They showed the same tendency as those of Example 1. The mixtures had the slightly lower spinnabilities than block-copolyetheresters alone as the Example 1. This problem attributable to phase separation of the polymers, but it was successfully solved by increasing the polyether content in block-copolyetheresters and decreasing that in the mixtures.

EXAMPLE 3

Block-copolyetheresters were prepared from the dimethyl terephthalate and isophthalate fixed at a ratio of 80/20 by weight in place of the dimethyl terephthalate of the polyesters of Example 1 in the same manner as the Example 1 so that polyester/polyether segment ratio by weight becomes 85/15 and pelletized.

Next, diapers were manufactured in the same manner as the Example 1 and evaluated. The results of this evaluation were good as indicated by No. 18 in Table 2.

EXAMPLE 4

The two kinds of fiber diapers having a mean fiber size of 0.2 denier and a weight of 70 gr./m² and 400 gr./m² were prepared from the pellets having the polyester/polyether segment ratios of 85/15 and 0.5/5 by weight that was obtained for Example 1. The latter was sandwiched between cotton broad cloths (both warp and weft were 40S spun yarn, warp density was 120 fibers/inch, weft density was 60 fibers/inch) and quilted at an interval of 2-inch. The 1.2 m-wide and 2 m-long cut pieces of this quilting was rimmed and sewn into a bed pad.

The bed pad showed a high water absorption performance, a high shape retention and a higher heat insulation performance than conventional cotton ones to gain a high reputation when used and washed by method C repeatedly 50 times in ordinary households.

The former, on the other hand, was sandwiched between cotton broad side cloths (both warp and weft were 40S spun yarn, warp density was 95 fibers/inch, weft density was 59 fibers/inch) quilted at an interval of 1-inch. A sports underpant was manufactured from this quilting. It provided more comfortable feeling than conventional ones notwithstanding the perspiration in intensified motion and showed a high sliding abrasion resistance. It little decreased in performance and shape retention to gain a high reputation when used and washed by method A repeatedly 50 times.

EXAMPLE 5

Three types of block-polyetherester were prepared using polyethylene glycols having molecular weight 2000 (PEG-2000) (No. 19), molecular weight 1000 (PEG-1000) (No. 20) and molecular weight 600 (PEG-600) (No. 21) instead of polyethylene glycol having a molecular weight of 2,000 (PEG-2000) of Example 1, No. 4. Each poly-etherester was melt-blown and was made to diapers in the same manner as Example 1 and the results are shown in Table 3. Their spinnabilities and durabilities against household and laundry washing were almost the same as those of Example 1, No. 4.

EXAMPLE 6

Block-polyetherester was prepared in the same manner as Example 5, No. 2 except adding, as heat stabilizer, calcium acetate, phosphorous acid and 1,3,5-tris(3,5-di-t-butyl-4-hydroxybenzyl)benzene (0.15, 0.15 and 0.5 wt % respectively based on the total weight of the polymer). The poly-etherester was melt-blown and was made to diapers in the same manner as Example 1 and the results are shown in Table 3. Its spinnability and durability against household and laundry washing were almost the same as those of Example 1, No. 4.

TABLE 3

| | Block-copolyetheresters | | Heat stabilizer | Mean fiber size (denier) | Web Weight (gr./m²) | Spin-ability | Household washing 100 times | | | | |
|---|---|---|---|---|---|---|---|---|---|---|---|
| No. | Polyester segment | Polyether segment | | | | | Water absorption rate, method A | Water absorption rate, method B | Water holding capacity method A | Water holding capacity method B | Shape retention |
| 19 | 85% | 15% | 1.0 | 0.23 | 600 | Good | <1 | 11 | 125 | 6.4 | Good |
| 20 | 85 | 15 | 1.0 | 0.25 | 595 | Good | <1 | 12 | 128 | 6.7 | Good |
| 21 | 85 | 15 | 1.0 | 0.21 | 600 | Good | <1 | 13 | 127 | 6.2 | Good |
| 22 | 85 | 515 | 0.8 | 0.20 | 605 | Good | <1 | 12 | 122 | 6.6 | Good |

| | Laundry washing 100 times | | | | |
|---|---|---|---|---|---|
| No. | Water absorption rate, method A | Water absorption rate, method B | Water holding capacity method A | Water holding capacity method B | Shape retention |
| 19 | 1 | 13 | 122 | 6.3 | Good |
| 20 | 1 | 16 | 125 | 6.2 | Good |
| 21 | <1 | 15 | 119 | 6.5 | Good |
| 22 | 1 | 15 | 123 | 6.2 | Good |

We claim:

1. A melt-blow water-absorbing web of fibers whose main component is a block-copolyetherester having a polyester segment and a polyether segment therein, with said polyether segment comprising 5 to 80 wt % of the total weight of said blockcopolyetherester.

2. The melt-blow water-absorbing web of fibers as claimed in claim 1, wherein said melt-blow web of fibers is manufactured from a mixture of said block-copolyetherester and other organic polymers.

3. The melt-blow water-absorbing web of fibers as claimed in claim 1, wherein said melt-blow web of fibers is manufactured from said block-copolyetherester containing about 5 to 30 wt % of polyethers.

4. The melt-blow water-absorbing web of fibers as claimed in claim 1, wherein heat stabilizers are blended at the ratios of 0.05 to 10 wt % to said main component thereof.

5. The melt-blow water-absorbing web of fibers as claimed in claim 2, wherein said other organic polymers are polyesters.

6. The melt-blow water-absorbing web of fibers as claimed in claim 2, wherein said other organic polymer is one at least being selected out of polyalkylene glycol, and polyalkylene oxide.

7. The melt-blow water-absorbing web of fibers as claimed in claim 1, wherein said polyester segment is polybutyleneterephthalate.

8. The melt-blow water-absorbing web of fibers as claimed in claim 1, wherein said polyester segment is polyethyleneterephthalate.

9. The melt-blow water-absorbing web of fibers as claimed in claim 1, wherein said polyether segment is polyalkyleneglycol.

10. The melt-blow water-absorbing web of fibers as claimed in claim 1, wherein said polyether segment is polyalkyleneglycol.

11. The melt-blow water-absorbing web of fibers as claimed in claim 1, wherein said polyether segment is polyethyleneglycol.

12. The melt-blow water-absorbing web of fibers as claimed in claim 1, wherein said melt-blow web of fibers is manufactured from a mixture of said block-copolyester and alkylbenzene sulfonate.

* * * * *